United States Patent [19]

Allersma et al.

[11] 4,331,023

[45] May 25, 1982

[54] ADDITION AND MEASUREMENT OF GASES DISSOLVED IN MOLTEN METALS

[75] Inventors: Ties Allersma, Pittsburgh; James E. Simpson, New Kensington, both of Pa.

[73] Assignee: PPG Industries, Inc., Pittsburgh, Pa.

[21] Appl. No.: 129,138

[22] Filed: Mar. 10, 1980

Related U.S. Application Data

[62] Division of Ser. No. 968,604, Dec. 11, 1978, Pat. No. 4,239,532.

[51] Int. Cl.³ .................. G01N 7/00; G01N 27/26
[52] U.S. Cl. .................................... 73/19; 73/23; 204/195 P
[58] Field of Search ............... 73/19, 23; 204/195, 204/296

[56] References Cited

U.S. PATENT DOCUMENTS

| | | | |
|---|---|---|---|
| 2,411,157 | 11/1946 | Fene | 23/257 |
| 3,743,588 | 7/1973 | Brown | 204/195 M |
| 3,795,500 | 3/1974 | Murphy | 65/182 R |
| 3,855,098 | 12/1974 | Fletcher | 204/195 G |
| 3,896,020 | 7/1975 | Le Blanc | 204/195 M |
| 3,934,470 | 1/1976 | Amati | 75/60 |
| 4,003,818 | 1/1977 | Juillard | 204/296 |
| 4,092,844 | 6/1978 | Oertle | 73/19 |
| 4,223,549 | 9/1980 | Kitzinger | 73/19 |

*Primary Examiner*—P. D. Rosenberg
*Attorney, Agent, or Firm*—Donald Carl Lepiane

[57] ABSTRACT

Method and apparatus for measuring gases dissolved in molten metal. Also disclosed are method and apparatus for dissolving gases in molten metal and a method of forming a gas permeable but molten metal impervious ceramic tube. A ceramic member is leached by an invention process so as to be selectively gas permeable. The member is inserted into molten metal to submerge the permeable portion. Then a vacuum is applied to the member and dissolved gases are measured by the change in pressure caused by gases entering from the molten metal. In another embodiment gas is applied to the submerged member to cause it to dissolve in the molten metal.

11 Claims, 3 Drawing Figures

ADDITION AND MEASUREMENT OF GASES DISSOLVED IN MOLTEN METALS

This is a division of application Ser. No. 968,604, filed Dec. 11, 1978 now U.S. Pat. No. 4,239,532.

BACKGROUND OF THE INVENTION

1. Field of the Invention

This invention relates to the measurement of gases dissolved in molten metals. In particular, the instant invention relates to the measurement of hydrogen dissolved in the molten tin bath of a forming chamber used in float glass formation.

2. Prior Art

The formation of glass via the process wherein molten glass is cooled and formed into sheets while on the surface of a molten metal in a forming chamber is well known. It has been perceived that the composition of the molten metal on which the glass is formed may change as gases from the atmosphere and from the glass are dissolved into the molten metal. However, there has been no satisfactory way of measuring the amount of dissolved gas in the molten metal. Without knowledge of dissolved gas in the molten metal, it has not been possible to determine the effects of the changes in the gaseous atmosphere of the forming chamber on the molten metal. The forming chamber generally is maintained with an atmosphere of predominantly nitrogen with some hydrogen. This atmosphere is to prevent oxidation of the tin which is the conventional metal utilized in the forming chamber. The following references are considered pertinent to the apparatus and method of the instant invention.

U.S. Pat. No. 3,855,098 to Fletcher discloses an ionic sensitive electrode comprising a porous inert material of ceramic which carries on its surface a thin ion sensitive membrane to be exposed to a test liquid to develop an electrical potential as the function of the ionic activity or concentration of the test liquid. The porous material provides a mechanical support for the membrane and the porosity of the material serves to define continuous channels to carry electrolyte liquid to the interior surface of the membrane.

In U.S. Pat. No. 2,106,744 to Hood et al and U.S. Pat. No. 3,923,688 to Hammel et al disclose leaching to form porous glasses. However, selectively porous glasses do not have good thermal shock resistance as the porous portions have different thermal expansion characteristics.

U.S. Pat. No. 4,003,818 to Juillard et al discloses a method of obtaining a microporous membrane. The membrane is formed by formation of a paste which has a filler substance which may be removed after the article is formed from the paste. The pore-forming material is removed by solvent or chemical decomposition and may be calcium carbonate, colloidal alumina, metallic oxide or other products capable of solvent or chemical removal.

U.S. Pat. No. 3,896,020 to Le Blanc, Jr. discloses a sensor for measurement of carbon dioxide partial pressure in an aqueous electrolyte solution. The system of Le Blanc, Jr. is limited in that the system is specific to carbon dioxide. Further, the system in using organic materials in several layers is not suitable for high temperature use because of both thermal shock problems and difficulties with decomposition of the organic materials.

Porous sintered ceramic bodies are known, but these can not be formed to be selectively porous such that one portion of a unitary body is gas pervious while another portion is gas impervious.

There is a need for a device for measuring the partial pressure of gas in molten metals that is resistant to thermal shock, easily inserted in the metal, capable of withstanding high temperatures and inexpensive. Presently, there are no systems known to the applicant for accurately measuring partial pressure of gas in a molten metal while the metal remains molten. Further, there is a need for a device to measure partial pressure of gases in the bath of a glass-forming chamber in order to aid in a determination of bath chemistry as it relates to the balancing of bath atmosphere and gaseous additions to the bath. Further, there is a need for a device that permits dissolving gases in a bath by means other than providing an atmosphere above the bath. Further, there is a need for formation of a permeable ceramic body that will allow gases to permeate the body but not allow metals to penetrate.

SUMMARY OF THE INVENTION

It is an object of this invention to overcome disadvantages of prior apparatus and processes.

It is another object of this invention to measure the partial pressure of gases in molten metal.

It is a further object of this invention to provide means for dissolving gases in molten metals.

It is another additional object of this invention to provide a selectively permeable high temperature shock-resistant material.

It is a further object of this invention to allow control of gases dissolved in the bath of a glass-forming chamber.

These and other objects of the instant invention are generally accomplished by providing a selectively permeable hollow ceramic member. The ceramic member is immersed such that the permeable portion is entirely beneath the surface of the metal. A vacuum is then drawn on the hollow ceramic body. The hollow body is then sealed and changes in interior pressure as the gases from the molten metal enter the hollow member are measured by a measuring device connected to the hollow ceramic member. The hollow ceramic member is formed by selectively dissolving glassy portions of the ceramic body to make it permeable to gases but not permeable to molten metals. In another embodiment of the invention, gases may be dissolved into molten metal by introducing gas into the hollow member after it is inserted in the molten metal such that gases exit from the member into the molten metal and are dissolved. The pressure of the gas introduced in such that gas does not bubble from the tube, but creates a gas-molten metal interface.

In a best mode of the invention, a closed end ceramic tube of 85 percent mullite and 15 percent glass is immersed from the closed end about 2 inches into a solution of about 20 percent by weight hydrofluoric acid, about 2 percent by weight nitric acid and the balance water by weight. After leaching for about 2 days, the tubular member is withdrawn, rinsed and dried. The tubular member then is connected with apparatus that is capable of drawing a vacuum in the tube, isolating the tube with the vacuum and has a pressure measuring and indicating device to read the change in partial pressure after isolation as gases enter from the molten metal. The apparatus is arranged so that the leached portion of the mullite tube is completely immersed in the tin of the molten metal bath of a glass-forming chamber. A vacuum is drawn on the tube, the tube is isolated and the final pressure is read from the pressure measuring device.

DETAILED DESCRIPTION OF THE INVENTION

The instant invention, as summarized above, encompasses several parts. The invention relates to apparatus for measuring dissolved gases in molten metals. The invention further relates to apparatus for carrying out the dissolving of gases in metals. The invention further comprises the formation of a novel selectively porous ceramic member which forms a part of the apparatus for measuring dissolved gases or dissolving gases into molten metal. The invention will be further described with reference to FIGS. 1 and 2 which illustrate the invention for measuring the amount of dissolved gas in molten metal and the addition of gases to molten metal, respectively.

Figure 1:
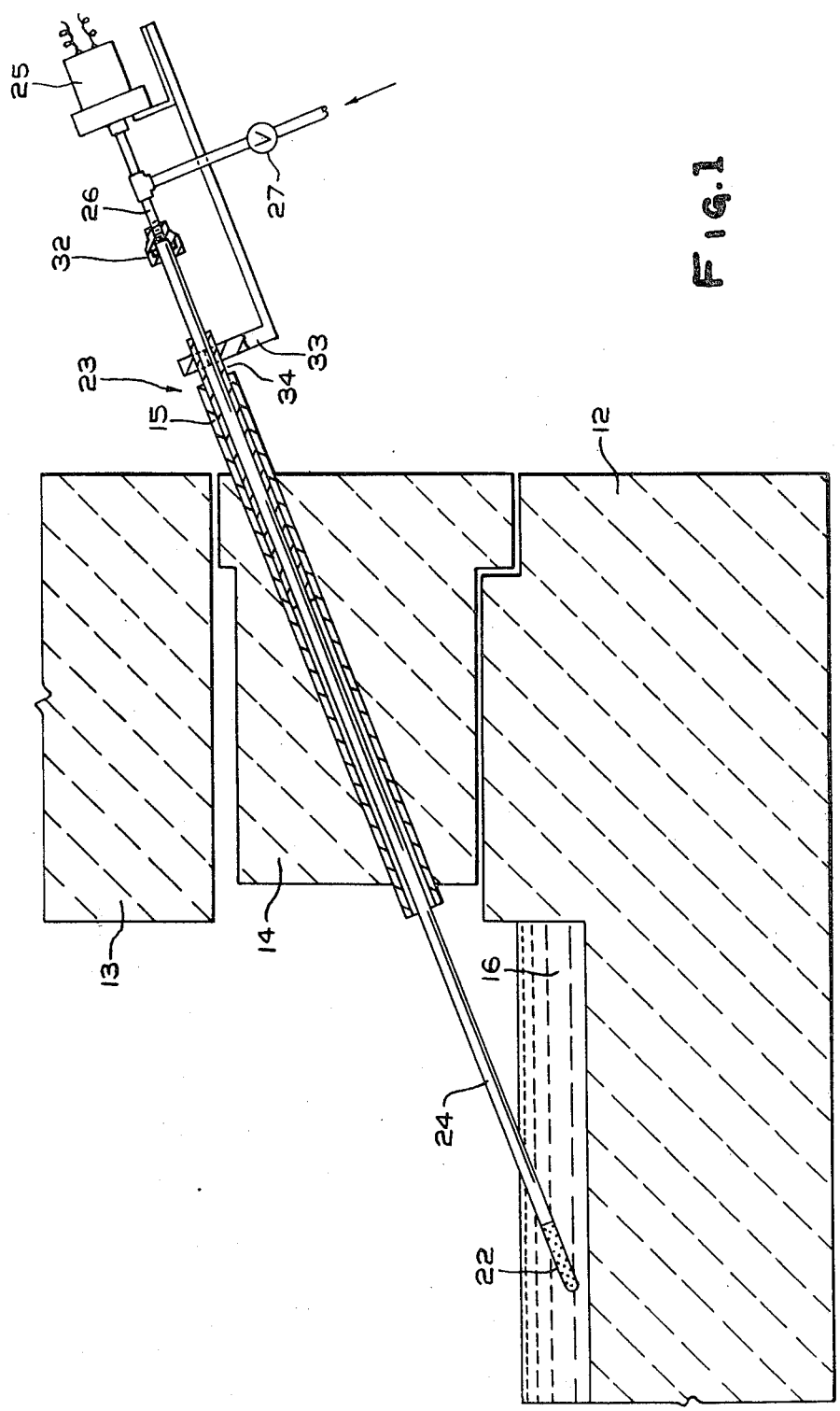
FIG. 1 illustrates in partial cross-section the apparatus of the invention utilizing the novel selectively permeable ceramic member for measurement of partial pressure of hydrogen in the molten metal bath of a glass-forming chamber.
Figure 2:
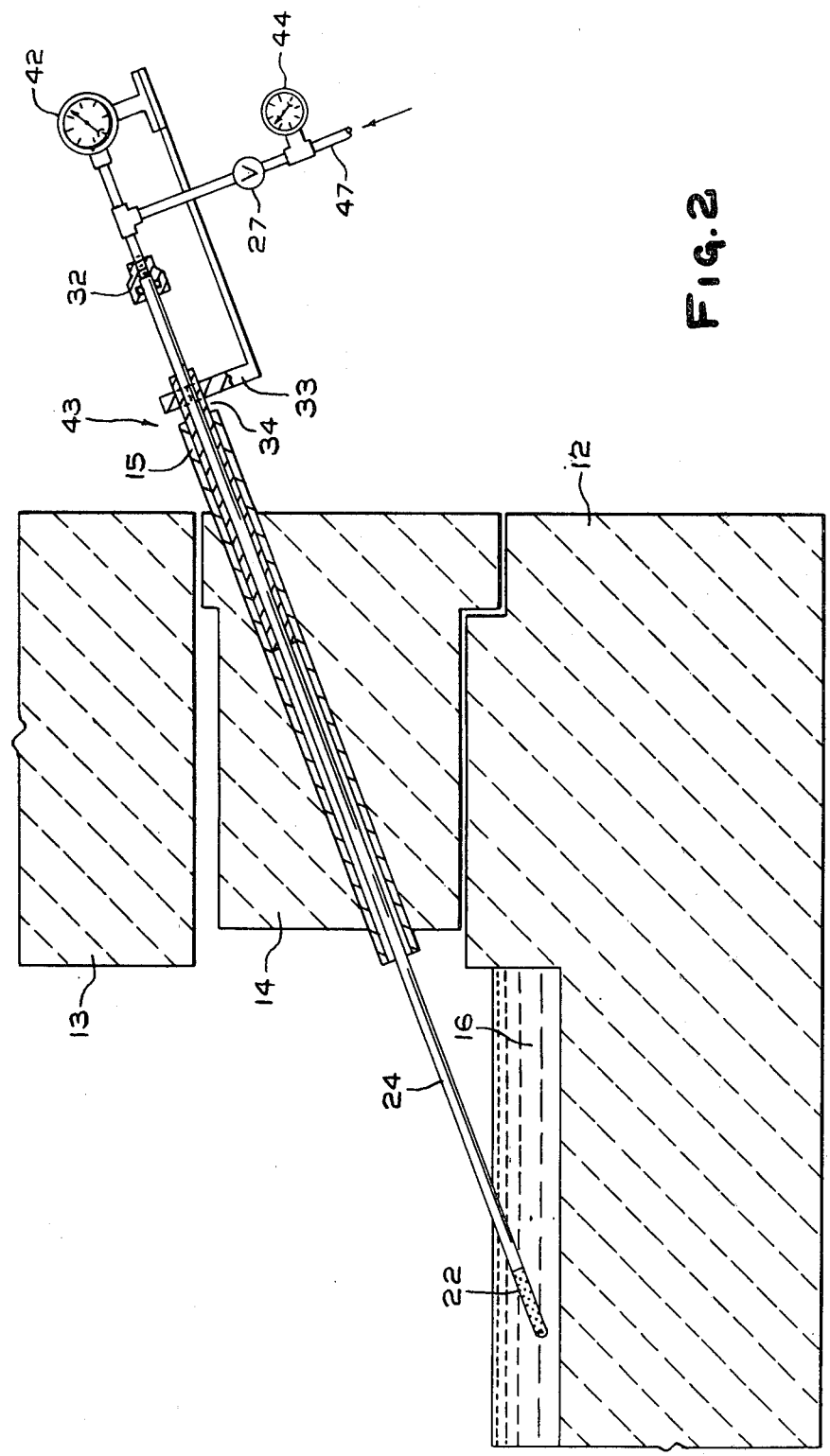
FIG. 2 illustrates in partial cross-section the apparatus of the invention for dissolving gases in molten metal.

The invention as illustrated in FIGS. 1 and 2 represents the use of the apparatus in combination with the forming chamber of a float glass formation process. In the formation of glass via the float formation process, the molten glass is allowed to flow from a furnace onto a pool or bath of molten metal. On the pool of molten metal in the forming chamber, the molten glass is stretched and cooled as it passes through the forming chamber to result in a glass sheet. The molten glass generally also is subjected to lateral stretching forces to produce glass thinner than equilibrium thickness or to lateral compressive forces that aid in production of glass thicker than equilibrium thickness. The float formation of glass sheets is well known and reference may be had to U.S. Pat. Nos. 3,083,551 and 3,215,516, both to Pilkington, for descriptions of the formation of glass on molten tin. As illustrated in FIGS. 1 and 2, the forming chamber bottom member 12 contains the molten metal bath 16. The apparatus of the invention generally indicated as 23 in FIG. 1 and 43 in FIG. 2 passes through a side seal block 14. The side seal block 14 occupies the space between the roof 13 of the furnace and the bottom member 14 of the furnace. The use of side seal blocks between the bottom member and roof of the furnace is known in the art.

The side seal block 14 is drilled and a sleeve of iron 15 is mounted in the side seal to allow insertion and removal of the probe 24. As illustrated, the probe is composed of a closed end tube having a gas-permeable end 22. The remainder of the tube 24 is impermeable to both gas and molten metal.

As illustrated in FIG. 1, the tube 24 is connected by gas-tight seal 32 to pipe 26. The pipe is in turn connected past valve 27 to a source of vacuum, not shown. The probe is mounted on frame 33 which in cooperation with sleeve 34 maintains the probe in a rigid position during use. The apparatus further comprises transducer 25. The transducer 25 has the capacity to sense changes in pressure within the apparatus. In operation, valve 27 is open and a vacuum is applied to achieve a partial pressure of less than about one millimeter of mercury. Valve 27 is then closed and the change in pressure is sensed as hydrogen enters the tube. The bath atmosphere of the forming chamber preferably is composed almost exclusively of nitrogen with a small amount of hydrogen and unintentional traces of oxygen, water and hydrogen sulfide. Nitrogen does not appreciably dissolve in tin and therefore the pressure reading may be considered as the result of hydrogen entering the probe. The gas has been tested and is almost pure hydrogen. Over a period of time, the transducer is read to determine the change in pressure within the probe as hydrogen enters from the molten metal bath. After a period of time the pressure in the probe will no longer increase and then equals the partial pressure in the molten metal. The concentration $C_p$ of the hydrogen, expressed in grams per 100 grams of metal, is equal to the product of the solubility and the square root of the partial pressure expressed in atmospheres. The solubility is the concentration of hydrogen in the molten metal in equilibrium with hydrogen at atmospheric pressure and specific values may be found in the literature, for example Bever and Floe (Am. Inst. Mining and Met. Eng. 156, 149 (1944). The solubility is temperature dependent; at 1000° C. it is approximately $3.6 \times 10^{-6}$ g/100 g. The length of time the readings may be maintained is limited by the effectiveness of seal 32 and valve 27 in excluding other gases.

While the invention has been illustrated with a pressure transducer to measure pressure change, other types of devices could also be utilized. Among pressure sensing devices suitable for the invention are manometers, diaphragm vacuum gauges and ion pumps. A preferred transducer is the Viatran Model No. 218 manufactured by Viatran Corporation, Grand Island, NY.

As illustrated in FIG. 2, the invention also encompasses the use of the novel selectively porous member for a dissolver of gas into molten metal. The utilization of the device in this way allows more efficient placement of dissolved hydrogen into the molten metal bath than the present method of dissolving from an overhead atmosphere containing hydrogen. In the apparatus of FIG. 2, the valve 27 allows feeding of gases through pipe 47 into the molten metal. Bottled gas may be utilized as a source of pure gas under pressure. Gauge 44 measures the volume of gas passing into the probe. Control gauge 42 regulates the pressure under which the gas is applied to the molten metal. The pressure preferably is controlled such that the gas does not bubble into the molten metal but is dissolved as it exits from the probe. The device may be utilized as a bubbler if mixing is desired in the molten metal.

Figure 3:
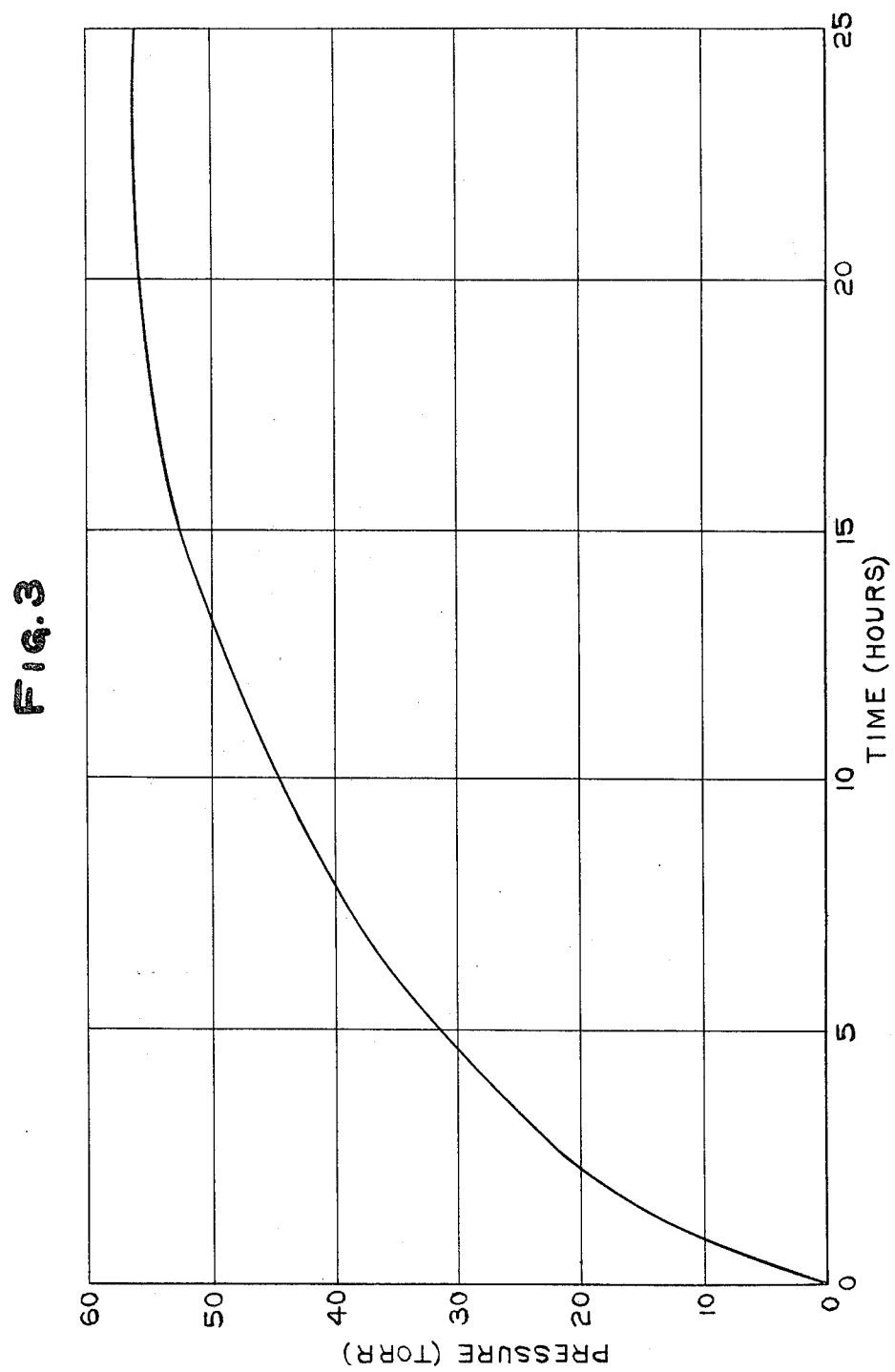
FIG. 3 illustrates in graph form readings measured with apparatus of the invention.

The illustration of FIG. 3 represents the type of measurements which are possible with the dissolved gas measurement apparatus of the invention. The illustration represents the data obtained from a laboratory experiment in which an atmosphere of about 7% hydrogen with the balance nitrogen was maintained over molten tin. The dissolved concentration may be calculated as set out above. One torr equals 1 mm. of mercury or 1/760 of a standard sea level atmosphere.

The probe may be constructed of any material which possesses a phase which may be leached leaving an integral device permeable to gases but not to molten metal. As used herein the term integral means that the ceramic body while having permeable and impermeable portions does not have a seam or joint between the portions. Materials suitable for the instant invention will have thermal expansion characteristics which remain substantially the same after leaching as before in order to create a thermal shock-resistant article. Among suitable materials for the probe of the invention are ceramic composites of mullite and silica. The mullite particles or crystals of such a composite have a felt-like packing which when leached results in a strong but porous article. Among other leachable materials are tubes of alumina and silica such as those of 90% alumina and 10% silicon dioxide. A preferred ceramic material comprises about 80-85 percent mullite (aluminum silicate) and about 15-20 percent silica glass ($SiO_2$). Leaching of the preferred material results in an article of high thermal shock resistance and good permeability to gas but an article not permeable to molten metal. The 85/15 mullite-silica glass composite has almost the same thermal expansion after leaching as before leaching. It is theorized that this is the reason that the leached body has good shock resistance. The coefficient of expansion has been measured with a quartz pushrod dilatometer between 25° C. and 300° C. as $3.9 \times 10^6/°C$. before leaching and $4.3 \times 10^6/°C$. after leaching. Further, is is necessary that the ceramic article utilized for the instant invention not be gas permeable prior to leaching. The preferred mullite-glass ceramic body is formed by firing a body formed by casting or pressing processes. The preferred material further has the advantage that it is machineable both prior to and subsequent to leaching.

The material selected to leach the leachable phase of a ceramic body for the instant invention may be any corrosive material for a minor phase. For use with the preferred mullite and glass article, a leachant solution of about 20 percent hydrofluoric acid, about 2 percent nitric acid and the balance water has been found to be suitable. Such a solution results in substantially complete removal of the glassy phase in a relatively short time. For example, an MV30 closed end tube from McDanel Refractories, Beaver Falls, Pa., formed of 85 percent mullite and 15 percent glass with an outside diameter of about 9.5 mm. and a wall thickness of about 1.7 millimeter was leached in about 24 hours. The tube is wrapped in tape and/or covered with rubber cement at a point about 2 inches from the end and then submerged in the acid solution until about a 2 inch portion at the end becomes permeable. The tube is then rinsed with water. Optionally, the surface of the tube may be further smoothed above the leached portion to prevent gas creeping along the tube from the surface of the tin to the porous portion.

While the instant invention has been described as primarily utilized for molten tin, the gas measuring or adding probe of the instant invention could also be utilized with other molten metals such as zinc, mercury, lead, copper, aluminum or iron. The invention further could be practiced with other materials by selection of ceramics of higher temperature or corrosion resistance. For instance, the process and apparatus of the instant invention could be utilized for measurement of gases or addition of gases to molten ceramic and hot or corrosive chemical materials.

The apparatus, selectively porous ceramic body and method of formation of the selective permeable ceramic body have numerous advantages. Among other advantages are that the member having selectively located permeable portions has high mechanical strength after formation of the permeable portion. Further, integral bodies having several permeable and impermeable parts can be made by only exposing selective parts to the acid solution. An additional advantage is that the articles of the instant invention have good thermal shock resistance as the expansion characteristics of each portion remain substantially the same. Another advantage of integral bodies is that the impermeable and permeable materials retain the ability to be shaped, such as by machining or filing after formation.

Although this invention has been described with reference to particularly preferred embodiments, those skilled in the art of instrumentation involving molten metals will recognize that variations may be made in the practice of this invention without departing from the concepts disclosed here. For instance, while the instant invention is described with a probe in the shape of a closed end tube, the shape of the probe could be selected such that it was formed of another shape or the location of the permeable portion could be varied such as in the form of a ring around the probe rather than encompassing the entire bottom portion of the probe. Accordingly, this disclosure is intended to be illustrative rather than limiting and the inventors have defined their invention in the accompanying claims.

We claim:
1. A method of measuring the amount of at least one gas dissolved in a liquid comprising the steps of:
providing a probe having a unitary outer wall to define a passageway within the probe, the outer wall has a portion to be submerged in the liquid which portion is substantially permeable with respect to the at least one gas but substantially impermeable to the liquid containing the at least one gas and has the remaining wall portion substantially impermeable with respect to both the at least one gas and liquid;
submerging at least the permeable outer wall portion of the probe in the liquid having the at least one gas; and
measuring gas pressure in the probe to monitor gas passing through the permeable outer wall portion of the probe.
2. The method as set forth in claim 1 wherein said measuring step includes the steps of:
subjecting the passageway within the probe to a vacuum; and
monitoring change in gas pressure caused by the at least one gas entering the passageway from the liquid.
3. The method as set forth in claim 2 wherein said subjecting step is practiced prior to said monitoring step.
4. The method as set forth in claim 2 wherein said probe comprises a ceramic material.
5. The method as set forth in claim 1 wherein the liquid is molten metal comprising tin.
6. The method as set forth in claim 5 wherein the molten metal forms metal bath in a chamber for glass formation.
7. The method as set forth in claim 6 wherein said submerging step includes the step of inserting the probe through side of the glass-forming chamber into the molten metal bath.
8. The method as set forth in claim 1 or 6 wherein the at least one gas is hydrogen.

9. The method as set forth in claim 1 wherein said measuring step is accomplished by measuring partial pressure.

10. The method as set forth in claim 1 wherein the outer wall portion impermeable with respect to both the at least one gas and liquid comprises mullite and glassy material and the outer wall portion permeable with respect to the at least one gas but impermeable to the liquid comprises mullite.

11. The method as set forth in claim 10 wherein the mullite and glassy material is about 80 weight percent mullite and about 20 weight percent silica dioxide.

* * * * *